US006790848B2

(12) United States Patent
Briggs et al.

(10) Patent No.: US 6,790,848 B2
(45) Date of Patent: Sep. 14, 2004

(54) 4-PIPERAZINYLINDOLE DERIVATIVES WITH 5-HT6 RECEPTOR AFFINITY

(75) Inventors: Andrew John Briggs, Mountain View, CA (US); Robin Douglas Clark, Palo Alto, CA (US); Ralph New Harris, III, Redwood City, CA (US); David Bruce Repke, Milpitas, CA (US); Douglas Leslie Wren, Palo Alto, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 118 days.

(21) Appl. No.: 10/172,360

(22) Filed: Jun. 14, 2002

(65) Prior Publication Data

US 2003/0045527 A1 Mar. 6, 2003

Related U.S. Application Data

(60) Provisional application No. 60/298,834, filed on Jun. 15, 2001, and provisional application No. 60/378,748, filed on May 8, 2002.

(51) Int. Cl.[7] ................... C07D 403/04; A61K 31/496; A61K 25/24; A61P 25/18
(52) U.S. Cl. ................... 514/254.09; 544/373
(58) Field of Search ...................... 514/254.09; 544/373

(56) References Cited

U.S. PATENT DOCUMENTS

| | | | |
|---|---|---|---|
| 5,696,122 A | 12/1997 | Gaster et al. | |
| 6,251,893 B1 | 6/2001 | Maddaford et al. | |
| 2002/0115670 A1 * | 8/2002 | Kelly et al. | 514/253.09 |
| 2002/0165251 A1 * | 11/2002 | Caldirola et al. | 514/305 |

FOREIGN PATENT DOCUMENTS

| | | |
|---|---|---|
| DE | 19934433 A1 | 1/2001 |
| EP | 0941994 A1 | 9/1999 |
| JP | 60-190761 A2 | 9/1985 |
| WO | WO96/03400 A1 | 2/1996 |
| WO | WO98/27081 A1 | 6/1998 |
| WO | WO01/32660 A1 | 5/2001 |
| WO | WO 02/08178 A1 | 1/2002 |
| WO | WO 02/32863 A1 | 4/2002 |
| WO | WO 02/36562 A2 | 5/2002 |
| WO | WO 02/41889 A2 | 5/2002 |
| WO | WO 2002/041889 A2 * | 5/2003 |

OTHER PUBLICATIONS

West, Anthony R., Solid State Chemistry and its Applications, Wiley, New York, 1988, pp. 358 & 365.*

Wolff, Manfred E. "Burger's Medicinal Chemistry, 5ed, Part I", John Wiley & Sons, 1995, pp. 975–977.*

Banker, G.S. et al, "Modern Pharmaceutics, 3ed.", Marcel Dekker, New York, 1996, pp. 451 and 596.*

Robichaud, A.J. et al, Ann. Reports Med. Chem., vol. 35, 2000, 11–19.*

Kelley, Provisional Application 60/245,118, 2000.*

Caldirola, Provisional Application 60/243,115, 2000.*

Monsma, Jr. Frederick J., et al., "Cloning and Expression of a Novel Serotonin Receptor with High Affinity for Tricyclic Psychotropic Drugs," *Molecular Pharmacology*, 1993, 43:320–327, The American Society for Pharmacology and Experimental Therapeutics.

Carlson, Rolf, et al., "Efficient Synthesis of Imines by a Modified Titanium Tetrachloride Procedure,"*Acta Chemica Scandinavica*, 1992, pp. 1211–1214, 46(12).

Matsumoto Masakatsu, et al., "A Facile Synthesis of 4-Oxo-4,5,6,7-Tetrahydroindoles,"*Heterocycles*, 1984, pp. 2313–2316, vol. 22, No. 10.

* cited by examiner

*Primary Examiner*—James O. Wilson
*Assistant Examiner*—Thomas McKenzie
(74) *Attorney, Agent, or Firm*—Robert C. Hall

(57) ABSTRACT

This invention relates to compounds which have generally 5-HT6 receptor affinity and which are represented by Formula I:

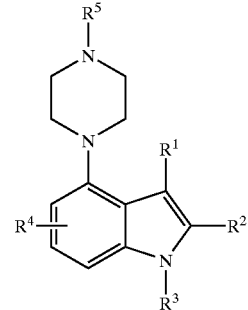

Formula I wherein $R^3$ is $SO_2$—Ar, Ar is aryl or heteroaryl; and $R^1$, $R^2$, $R^4$ and $R^5$ are as defined herein; or individual isomers, racemic or non-racemic mixtures of isomers, or pharmaceutically acceptable salts or solvates thereof. The invention further relates to pharmaceutical compositions containing such compounds, methods for their use as therapeutic agents, and methods of preparation thereof.

7 Claims, No Drawings

4-PIPERAZINYLINDOLE DERIVATIVES WITH 5-HT6 RECEPTOR AFFINITY

CROSS REFERENCE TO RELATED APPLICATIONS

Pursuant to 35 U.S.C. §119(e), this application claims priority to the filing dates of the U.S. Provisional Patent Applications Serial No. 60/298,834, filed Jun. 15, 2001, and Ser. No. 60/378,748, filed May 8, 2002, which are incorporated herein by reference in their entirety.

FIELD OF THE INVENTION

This invention relates to new 4-piperazinyl indole derivatives with 5-HT6 receptor affinity, and associated pharmaceutical compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5- HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nervous system disorders. In particular, 5-HT6 receptor selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. (See for ex. B. L. Roth et al., J. Pharmacol. Exp. Ther., 268, pages 1403–14120 (1994), D. R. Sibley et al., Mol. Pharmacol., 43, 320–327 (1993), A. J. Sleight et al, Neurotransmission, 11, 1–5 (1995), and A. J. Sleight et al. Serotonin ID Research Alert, 1997, 2 (3), 115–8).

Furthermore, the effect of 5-HT6 antagonist and 5-HT6 antisense oligonucleotides to reduce food intake in rats has been reported (Br J Pharmac. 1999 Suppl 126, page 66 and J Psychopharmacol Suppl A64 1997, page 255).

SUMMARY OF THE INVENTION

This invention relates to compounds comprising Formula I:

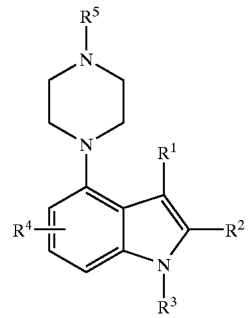

Formula I wherein:

$R^1$ is selected from hydrogen, halo, haloalkyl, and $C_{1-6}$-alkyl;

$R^2$ is selected from hydrogen, $C_{1-6}$-alkyl, $C_{1-6}$-alkoxy, and $C_{1-6}$-alkylthio;

$R^3$ is —$SO_2$—Ar, and Ar is selected from aryl and heteroaryl, optionally substituted with one or more substitutents selected from lower alkyl, lower alkoxy, thioalkyl, halo, haloalkyl, hydroxyalkyl, nitro, hydroxy, cyano, amino, alkylamino, dialkylamino, aminocarbonyl, carbonylamino, alkylsulfonyl, haloalkylsulfonyl, aminosulfonyl, and sulfonylamino;

$R^4$ is selected from hydrogen, halogen, $C_{1-6}$-alkyl, $C_{1-6}$-alkoxy, $C_{1-6}$-alkylthio, trifluoromethyl, cyano, and acyl; and $R^5$ is selected from hydrogen, $C_{1-6}$-alkyl and benzyl; or individual isomers, racemic or non racemic mixtures of isomers, prodrugs, or pharmaceutically acceptable salts or solvates thereof.

In another aspect, the invention relates to pharmaceutical compositions containing a therapeutically effective amount of at least one compound of Formula I, or individual isomers, racemic or non-racemic mixtures of isomers, or pharmaceutically acceptable salts or solvates thereof, in admixture with at least one suitable carrier.

In another aspect, this invention relates to a method of treatment of a disease in a mammal treatable by administration of compound of Formula I having a selective affinity to 5-HT6 receptor, in particular a method of treatment in a subject having a disease state comprising Alzheimer's disease, central nervous disorders, such as for example, psychoses, schizophrenia, manic depressions, neurological disorders, Parkinson's disease, amyotrophic lateral sclerosis and Huntington's disease. In another aspect, this invention relates to a method of treatment in a subject having a gastrointestinal disease comprising functional bowel disorder. Other disease states alleviated by 5-HT6 agonists, and therefore by the compounds of Formula I, are gastrointestinal diseases comprising irritable bowel syndrome (IBS), and obesity.

In a preferred embodiment, the invention further relates to a process which comprises:
treatment of a compound of formula f Formula f

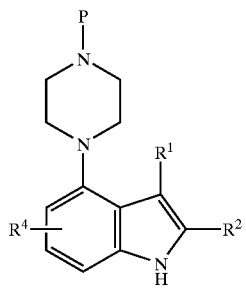

wherein P is a protective group and $R^1$, $R^2$ and $R^4$ are as defined herein, with an arylsulfonyl halide of Formula Ar—SO2-Hal wherein Hal is a halogen; followed by deprotection to provide a compound of general Formula I:

Formula I

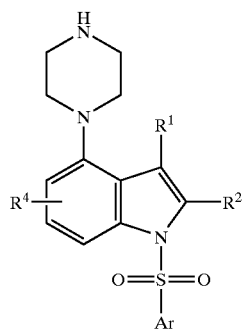

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a monovalent linear or branched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, octyl, dodecyl, and the like. "Alkyl" also means a cyclic or a combination of linear or branched, and cyclic saturated hydrocarbon radical consisting solely of carbon and hydrogen atoms, having from one to twelve carbon atoms inclusive, unless otherwise indicated. Examples of such alkyl radicals include but are not limited to, cyclopropyl, cyclopropylmethyl, cyclohexyl, cyclopropylethyl and the like.

"Lower alkyl" means a monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Alkylene" means a divalent linear or branched saturated hydrocarbon radical, consisting solely of carbon and hydrogen atoms, having from one to six carbons inclusive, unless otherwise indicated. Examples of alkylene radicals include, but are not limited to, methylene, ethylene, propylene, 2-methyl-propylene, butylene, 2-ethylbutylene, and the like.

"Alkoxy" means a radical —O—R, wherein R is a lower alkyl radical as defined herein. Examples of alkoxy radicals include, but are not limited to, methoxy, ethoxy, isopropoxy, and the like.

"Alkylthio" or "alkylsulfanyl" means a radical —SR, wherein R is a lower alkyl radical as defined herein. Examples of alkylthio radicals include, but are not limited to, methylthio, butylthio, and the like.

"Alkylsulfinyl" means a radical —SOR, wherein R is a lower alkyl radical as defined herein. Examples of alkylsulfinyl radicals include, but are not limited to, methylsulfinyl, ethylsulfinyl, and the like.

"Alkylsulfonyl" means a radical —$SO_2R$, wherein R is a lower alkyl radical as defined herein. Examples of alkylsulfonyl radicals include, but are not limited to, methylsulfonyl, ethylsulfonyl, and the like.

"Aryl" means a monovalent cyclic aromatic hydrocarbon radical consisting of one or more fused rings in which at least one ring is aromatic in nature, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, alkylsulfonyl, aminosulfonyl, and/or sulfonylamino, unless otherwise indicated. Examples of aryl radicals include, but are not limited to, phenyl, naphthyl, biphenyl, indanyl, anthraquinolyl, dichlorophenyl, bromophenyl, fluorophenyl, and the like.

"Halo" or "Halogen" means the radical fluoro, bromo, chloro, and/or iodo.

"Haloalkyl" means a lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Heteroaryl" means a monovalent aromatic carbocyclic radical having one or more rings incorporating one, two, three or four heteroatoms within the ring (chosen from nitrogen, oxygen, or sulfur) which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, alkylsulfonyl, aminosulfonyl, and/or sulfonylamino, unless otherwise indicated. Examples of heteroaryl radicals include, but are not limited to, imidazolyl, oxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, naphthyridinyl, and the like.

"Leaving group" means a group with the meaning conventionally associated with it in synthetic organic chemistry, i.e., an atom or group displaceable under alkylating conditions. Examples of leaving groups include, but are not limited to, halogen, alkyl- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Amino-protecting group" means a protecting group that refers to those organic groups intended to protect the nitrogen atom against undesirable reactions during synthetic procedures and includes, but is not limited to, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by mild acids in the case of BOC, e.g., trifluoroacetic acid or hydrochloric acid in ethyl acetate; or by catalytic hydrogenation in the case of CBZ.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Protective group" or "protecting group" means a group that selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, and methyl or alkyl ethers, and the like. Protective or blocking groups for carboxyl groups are similar to those described for hydroxyl groups, preferably tert-butyl, benzyl or methyl esters.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, maleic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, trifluoroacetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, the disease state being treated, the severity of the disease treated, the age and relative health of the subject, the route and form of administration, the judgement of the attending medical or veterinary practitioner, and other factors.

"Disease state" means any disease, condition, symptom, or indication.

Throughout the application the following abbreviations are used with the following meaning:

| Alk | Alkyl group |
|---|---|
| Bn | Benzyl group |
| Boc | N-tert-butoxycarbonyl |
| m-CPBA | m-Chloroperbenzoic acid |
| DMF | N,N-Dimethylformamide |
| DMSO | Dimethylsulfoxide |
| Hal | Halogen |
| L | Leaving group |
| Oxone ™ | Potassium peroxymonosulfate |
| P or P' | Protective group |
| THF | Tetrahydrofuran |

Nomenclature

The naming and numbering of the compounds of this invention is illustrated below:

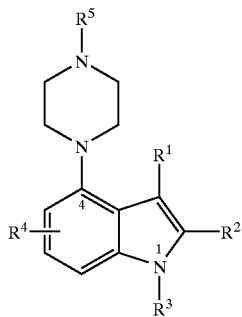

In general, the nomenclature used in this Application is based on AUTONOM™ v.4.0, a Beilstein Institute computerized system for the generation of IUPAC systematic nomenclature. However, because a strict adherence to these recommendations would result in the names changing substantially when only a single substituent is changed, compounds have been named in a manner that maintains consistency of nomenclature for the basic structure of the molecule.

For example, a compound of Formula I wherein $R^1$, $R^2$, $R^4$, and $R^5$ are hydrogen, and $R^3$ is naphthalenyl-1-sulfonyl, is named 1-(Naphthalene-1-sulfonyl)-4-piperazin-1-yl-1H-indole.

Preferred Compounds

Among compounds of the present invention set forth in the Summary of the Invention, certain compounds of Formula I, or individual isomers, racemic or non-racemic mixtures of isomers, or pharmaceutically acceptable salts or solvates thereof, are preferred:

$R^1$ is independently in each occurrence preferably hydrogen, halo, haloalkyl, or alkyl; preferably hydrogen or halo;

$R^2$ is independently in each occurrence preferably hydrogen, $C_{1-6}$-alkyl, $C_{1-6}$-alkoxy, or $C_{1-6}$-alkylthio; more preferably hydrogen or $C_{1-6}$-alkyl; and more preferably hydrogen;

$R^3$ is independently in each occurrence preferably —$SO_2$—Ar, wherein Ar is aryl or heteroaryl, more preferably arylsulfonyl;

$R^4$ is independently selected from hydrogen, halogen, $C_{1-6}$-alkyl, $C_{1-6}$-alkoxy, $C_{1-6}$alkylthio, trifluoromethyl, cyano, and acyl; and $R^5$ is preferably hydrogen or alkyl.

Exemplary particularly preferred compounds, or individual isomers, racemic or non-racemic mixtures of isomers, or pharmaceutically acceptable salts or solvates thereof, include:

1-(naphthalene-1-sulfonyl)-4-piperazin-1-yl-1H-indole;

1-(3,5-dichloro-benzenesulfonyl)-4-piperazin-1-yl-1H-indole;

1-(3-bromo-benzenesulfonyl)-4-piperazin-1-yl-1H-indole;

1-benzenesulfonyl-4-piperazin-1-yl-1H-indole;

4-piperazin-1-yl-1-(3-trifluoromethyl-benzenesulfonyl)-1H-indole;

4-piperazin-1-yl-1-(thiophene-2-sulfonyl)-1H-indole;

1-(4-methoxy-benzenesulfonyl)-4-piperazin-1-yl-1H-indole;

1-(4-fluoro-benzenesulfonyl)-4-piperazin-1-yl-1H-indole;

1-(4-fluoro-benzenesulfonyl)-4-(4-methyl-piperazin-1-yl)-1H-indole;

1-(4-ter-butyl-benzenesulfonyl)-4-piperazin-1-yl-1H-indole;

1-(4-methanesulfonyl-benzenesulfonyl)-4-piperazin-1-yl-1H-indole 1-(2,5-dichloro-benzenesulfonyl)-4-piperazin-1-yl-1H-indole;

1-(3-fluoro-benzenesulfonyl)-4-piperazin-1-yl-1H-indole;

1-(4-chloro-benzenesulfonyl)-4-piperazin-1-yl-1H-indole;

1-(2,5-dimethoxy-benzenesulfonyl)-4-piperazin-1-yl-1H-indole;

1-(3-methoxy-benzenesulfonyl)-4-piperazin-1-yl-1H-indole;

1-(3-chloro-benzenesulfonyl)-4-piperazin-1-yl-1Hindole;

1-(3-methanesulfonyl-benzenesulfonyl)-4-piperazin-1-yl-1Hindole;

1-(3-bromo-5-methanesulfonyl-benzenesulfonyl)-4-piperazin-1-yl-1H-indole;

1-(5-bromo-6-chloro-pyridine-3-sulfonyl)-4-piperazin-1-yl-1H-indole;

1-(2-fluoro-benzenesulfonyl)-4-piperazin-1-yl-1H-indole;

NN-dimethyl-3-(4-piperazin-1-yl-indole-1-sulfonyl)-benzenesulfonamide;

N-cyclopropyl-3-(4-piperazin-1-yl-indole-1-sulfonyl)-benzenesulfonamide;

1-(2-fluoro-5-methanesulfonyl-benzenesulfonyl)-4-piperazin-1-yl-1H-indole;

3-(4-piperazin-1-yl-indole-1-sulfonyl)-benzonitrile;

1-(2-methanesulfonyl-benzenesulfonyl)-4-piperazin-1-yl-1H-indole;

1-[3-(2-methyl-propane-1-sulfonyl)-benzenesulfonyl]-4-piperazin-1-yl-1H-indole;

1-(3-ethanesulfonyl-benzenesulfonyl)-4-piperazin-1-yl-1H-indole;

4-piperazin-1-yl-1-[3-(propane-1-sulfonyl)-benzenesulfonyl]-1H-indole;

1-(1-methyl-1H-imidazole-4-sulfonyl)-4-piperazin-1-yl-1H-indole;

1-(2,6-difluoro-benzenesulfonyl)-4-piperazin-1-yl-1H-indole;

1-benzenesulfonyl-3-bromo-4-piperazin-1-yl-1H-indole;

1-benzenesulfonyl-2-methyl-4-piperazin-1-yl-1H-indole; and 4-piperazin-1-yl-1-(3-trifluoromethanesulfonyl-benzenesulfonyl)-1H-indole.

It has been shown that compounds of formula I have a good affinity to the 5-HT6 receptor. The preferred compounds show a pKi>8.

| Compounds | pKi |
|---|---|
| 1-(Naphthalene-1-sulfonyl)-4-piperazin-1-yl-1H-indole | 9.8 |
| 1-(3,5-Dichloro-benzenesulfonyl)-4-piperazin-1-yl-1H-indole | 9.43 |
| 1-Benzenesulfonyl-4-piperazin-1-yl-1H-indole | 9.87 |
| 4-Piperazin-1-yl-1-(3-trifluoromethyl-benzenesulfonyl)-1H-indole | 9.70 |
| 4-Piperazin-1-yl-1-(thiophene-2-sulfonyl)-1H-indole | 9.35 |
| 1-(4-Methoxy-benzenesulfonyl)-4-piperazin-1-yl-1H-indole | 9.35 |
| 1-(4-Fluoro-benzenesulfonyl)-4-piperazin-1-yl-1H-indole | 8.86 |
| 1-(4-Fluoro-benzenesulfonyl)-4-(4-methyl-piperazin-1-yl)-1H-indole | 9.08 |
| 1-(4-ter-Butyl-benzenesulfonyl)-4-piperazin-1-yl-1H-indole | 8.45 |
| 1-(4-Methanesulfonyl-benzenesulfonyl)-4-piperazin-1-yl-1H-indole | 7.37 |
| 1-(2,5-Dichloro-benzenesulfonyl)-4-piperazin-1-yl-1H-indole | 9.82 |
| 1-(3-Fluoro-benzenesulfonyl)-4-piperazin-1-yl-1H-indole | 9.81 |
| 1-(4-Chloro-benzenesulfonyl)-4-piperazin-1-yl-1H-indole | 9.27 |
| 1-(2,5-Dimethoxy-benzenesulfonyl)-4-piperazin-1-yl-1H-indole | 9.03 |
| 1-(3-Methoxy-benzenesulfonyl)-4-piperazin-1-yl-1H-indole | 9.43 |
| 1-(3-Chloro-benzenesulfonyl)-4-piperazin-1-yl-1H-indole | 9.96 |
| 1-(3-Methanesulfonyl-benzenesulfonyl)-4-piperazin-1-yl-1H-indole | 8.57 |
| 1-(3-Bromo-5-methanesulfonyl-benzenesulfonyl)-4-piperazin-1-yl-1H-indole | 8.12 |
| 1-(5-Bromo-6-chloro-pyridine-3-sulfonyl)-4-piperazin-1-yl-1H-indole | 8.25 |
| 1-(2-Fluoro-benzenesulfonyl)-4-piperazin-1-yl-1H-indole | 10.28 |
| NN-Dimethyl-3-(4-piperazin-1-yl-indole-1-sulfonyl)-benzenesulfonamide | 8.69 |
| N-Cyclopropyl-3-(4-piperazin-1-yl-indole-1-sulfonyl)-benzenesulfonamide | 8.90 |
| 1-Benzenesulfonyl-3-bromo-4-piperazin-1-yl-1H-indole | 9.91 |
| 1-(2-Fluoro-5-methanesulfonyl-benzenesulfonyl)-4-piperazin-1-yl-1H-indole | 7.86 |
| 3-(4-Piperazin-1-yl-indole-1-sulfonyl)-benzonitrile | 8.95 |
| 1-(2-Methanesulfonyl-benzenesulfonyl)-4-piperazin-1-yl-1H-indole | 7.78 |
| 1-[3-(2-Methyl-propane-1-sulfonyl)-benzenesulfonyl]-4-piperazin-1-yl-1H-indole | 8.72 |
| 1-(3-Ethanesulfonyl-benzenesulfonyl)-4-piperazin-1-yl-1H!-indole | 8.81 |
| 4-Piperazin-1-yl-1-[3-(propane-1-sulfonyl)-benzenesulfonyl]-1H-indole | 8.81 |

General Synthetic Reaction Schemes

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1–15; *Rodd's Chemistry of Carbon Compounds,* Elsevier Science Publishers, 1989, Volumes 1–5 and Supplementals; and *Organic Reactions,* Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

In general, the compounds of Formula I are prepared following the method described in Schemes A or B.

Scheme A

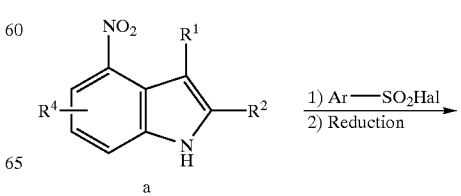

a

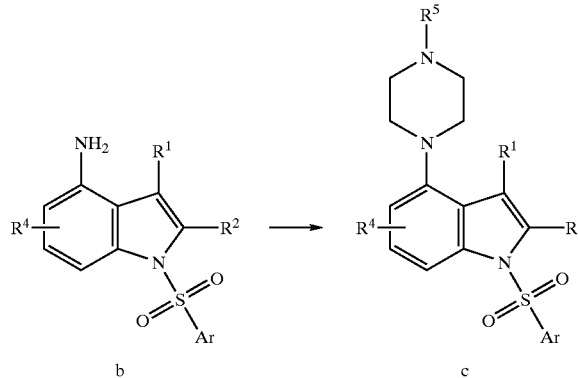

1-Arylsulfonyl-4-piperazinyl indoles of Formula c can be prepared by methods well known in the art, for example from 4-nitroindole of formula a by treatment with arylsulfonyl halide, preferably arylsulfonyl chloride, followed with reduction which can yield a 4-aminoindole of general formula b, which then can be treated with bis-chloroethylamine or a suitable derivative thereof.

tions as described herein. The arylsulfonyl indole of formula g can be prepared by treatment of the indole of formula f, wherein P is protecting group, with an arylsulfonyl halide, preferably arylsulfonyl chloride, in an inert solvent in the presence of a base. The indole of general formula f can be prepared by different methods, such as but not limited to, method A and method B.

In method A the piperazine indole of formula f can be prepared from the aminoindole of formula d by reaction of the amino group with bis-dichloroethylamine or a suitably protected derivative thereof as is well known in the art, as described for example in Mewshaw, R. et al. *Bioorg. Med. Chem. Lett.;* 8; 19; 1998; 2675–2680.

In method B the piperazine indole of formula f can be prepared from a protected 4-haloindole derivative e, wherein P' is a protecting group, preferably a triisopropylsilanyl protected 4-bromoindole by Palladium-catalyzed coupling with a suitably protected piperazine, such as Boc-piperazine (Buchwald reaction) or a benzyl piperazine. Removal of the indole protecting group by methods well known in the art, can yield the indole of Formula f.

Scheme B

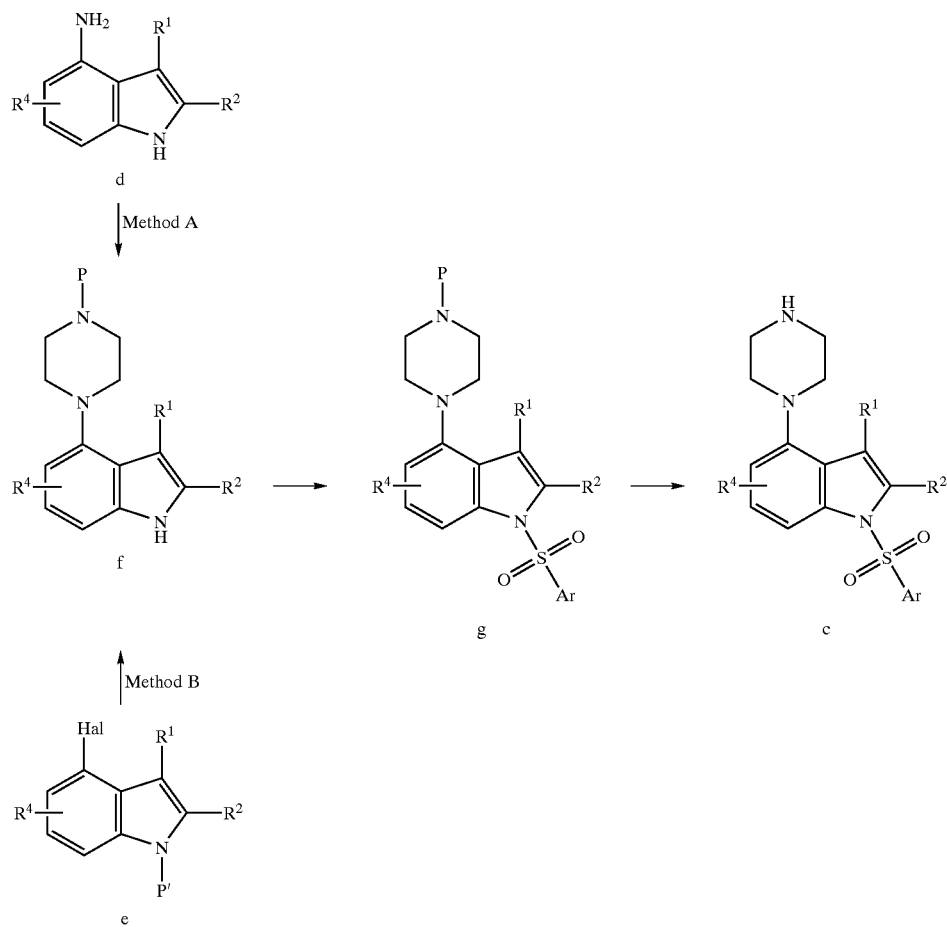

A 1-arylsulfonyl-4-piperazinyl indole of formula c can be prepared by removal of the protecting group P from 1-arylsulfonyl-4-piperazinyl indole g under standard condi-

SCHEME C

[Scheme C: synthesis pathway showing compounds q → p → m → i → h → c → c1, with intermediate structures and reagents including P-piperazine and R⁵]

An 1-arylsulfonyl-4-piperazinyl indole of formula c can be prepared by removing the protecting group P from an 1-arylsulfonyl-4-piperazinyl indole of formula h, in a solvent such as toluene and in the presence of e.g. hydrogen chloride gas. The arylsulfonyl indole of formula h can, on its turn, be prepared by treating at about 90° C. an arylsulfonyl-halo-tetrahydroindolone of formula i, such as an arylsulfonyl-chloro-tetrahydroindolone, with a protected piperazine, such as Boc-piperazine, in the presence of a catalyst like titanium tetrachloride and in a solvent like toluene. The arylsulfonyl-halo-tetrahydroindolone of formula i can, on its turn, be obtained by halogenating the corresponding arylsulfonyltetrahydroindolone of formula m in e.g. acetic acid/water 1:1 and in the presence of e.g. Cu(Hal)2, preferably CuCl2. The arylsulfonyltetrahydroindolone of formula m can be finally obtained by treating 1,5,6,7-tetrahydro-indol-4-one (formula p) with e.g. arylsulfonyl chloride in the presence of e.g. sodiumhydride, the reaction taking place at about 0° C. and in a solvent such as NMP or DMF.

1,5,6,7-tetrahydro-indol-4-one (formula p) can be finally obtained from 1,3 cyclohexane-dione (formula q) as described in example 4 (alternative).

If desired, the compound of general formula c can be converted into a compound of general formula c1 by alkylating the pyperidine rest by means of e.g. $R^5$-Hal and a conventional Lewis and/or Brönsted acid catalyst.

General Utility

The compounds of the invention have selective 5-HT6 receptor affinity and as such are expected to be useful in the treatment of certain CNS disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), schizophrenia, disorders associated with spinal trauma and/or head injury such as hydrocephalus, and withdrawal from drug abuse such as cocaine, ethanol, nicotine and benzodiazepines. Such compounds are also expected to be of use in the treatment of certain GI (gastrointestinal) disorders such as functional bowel disorder or irritable bowel syndrome (IBS), as well as for the treatment of obesity.

Testing

The pharmacology of the compounds of this invention was determined by art recognized procedures. The in vitro techniques for determining the affinities of test compounds for the 5-HT6 receptor in radioligand binding and functional assays are described in Example 14.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa. Representative pharmaceutical formulations containing a compound of the present invention are described in Examples 7–13.

EXAMPLES

The following preparations and examples are given to enable those skilled in the art to more clearly understand and to practice the present invention. They should not be considered as limiting the scope of the invention, but merely as being illustrative and representative thereof.

Example 1

1-(Naphthalene-1-sulfonyl)-4-piperazin-1-yl-1H-indole (1)

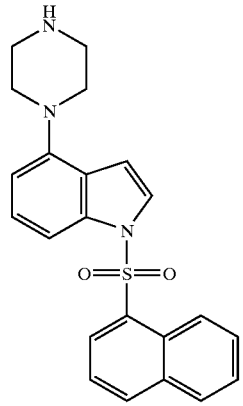

Step 1

1-(Naphthalene-1-sulfonyl)-4-nitro-1H-indole

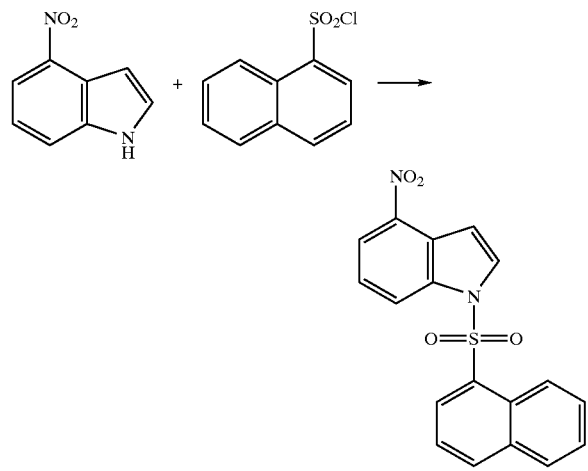

To a suspension of 370 mg (2.3 mmole) 4-nitro-1H-indole in 10 mL toluene was added 5 mL 4 M sodium hydroxide and 50 mg tetra-n-butyl ammonium hydrogen sulfate. Solid naphthalene-1-sulfonyl chloride (533 mg, 2.35 mmole) was added in one portion. The reaction mixture was stirred at room temperature for 0.25 hr. The mixture was diluted with 5 mL water and extracted with 25 mL ethyl ether. The organic phase was washed with 5 mL water, 5 mL saturated sodium chloride, dried (magnesium sulfate) and concentrated under reduced pressure. The residue was recrystallized from ether/hexane to provide 1-(naphthalene-1-sulfonyl)-4-nitro-1H-indole as light yellow crystals, 779 mg, m.p. 156–157° C.

Step 2

1-(Naphthalene-1-sulfonyl)-1H-indol-4-ylamine

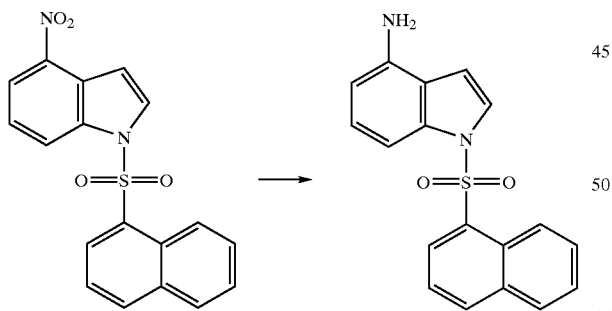

A mixture of 722 mg (1.97 mmole) 1-(naphthalene-1-sulfonyl)-4-nitro-1H-indole and 100 mg 10% palladium on carbon in 15 mL ethanol and 5 mL methanol was shaken under 40 psi hydrogen at room temperature for 4 hrs. The catalyst was removed by filtration and the filtrate was concentrated under reduced pressure. The residue was recrystallized from ether/hexane to provide 1-(naphthalene-1-sulfonyl) -1H-indol-4-ylamine as light yellow-green crystals, 480 mg, m.p. 133–134° C.

Step 3

1-(Naphthalene-1-sulfonyl)-4-piperazin-1-yl-1H-indole

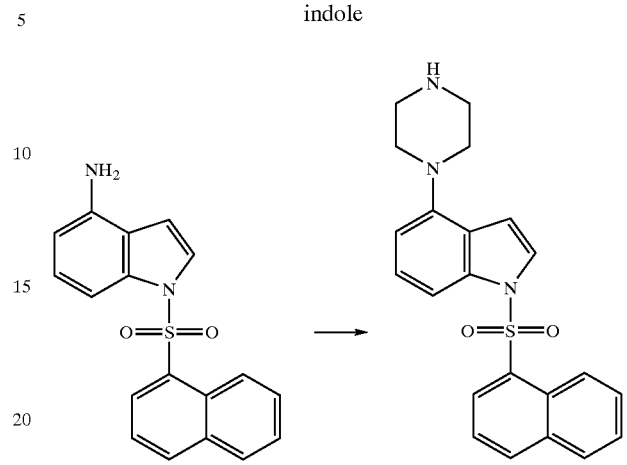

A mixture of 461 mg (1.43 mmole) 1-(naphthalene-1-sulfonyl)-1H-indol-4-ylamine, 255 mg (1.43 mmole) bis(2-chloroethyl)amine hydrochloride, and 0.5 mL diisopropylethylamine in 5 mL chlorobenzene was heated under reflux. After 4 hours, 0.25 mL diisopropylethylamine was added and heating under reflux was continued for 15 hours. The mixture was partitioned between 25 mL ethyl acetate and 10 mL 5% sodium hydroxide. The organic phase was washed with 5 mL saturated sodium chloride solution, dried (magnesium sulfate) and concentrated under reduced pressure. The residue was subjected to low pressure column chromatography over silica gel 230–400 mesh eluting with 8% methanol in chloroform. 1-(Naphthalene-1-sulfonyl)-4-piperazin-1-yl-1H-indole (1) was isolated as the hydrochloride salt from ethyl acetate/ether, 54 mg, M+H=392.

Example 2

1-(3,5-Dichloro-benzenesulfonyl)-4-piperazin-1-yl-1H-indole (2)

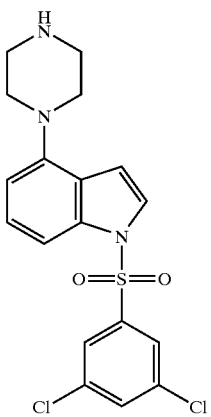

Step 1
4-(4-Benzyl-piperazin-1-yl)-1H-indole
Method A

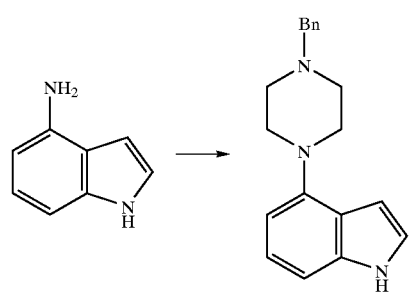

A mixture of 500 mg (3.78 mmole) 1H-indol-4-yl-amine, 993 mg (3.78 mmole) N-benzyl-bis(2-chloroethyl)amine hydrochloride, and 1.32 mL (7.6 mmole) diisopropylethylamine in 10 mL chlorobenzene was heated at 130° C. for 24 hours. Another 0.66 mL (3.8 mmole) diisopropylethylamine was added and the mixture was heated at 130° C. for an additional 5 hours. The mixture was partitioned between 25 mL ethyl acetate and 10 mL 5% sodium hydroxide. The organic phase was extracted with 10 mL 3 N hydrochloric acid. The aqueous phase was washed with 15 mL ethyl ether, then made basic with 50% sodium hydroxide. The product was extracted with 25 mL dichloromethane, the organic phase was washed with 10 mL water, dried (magnesium sulfate) and concentrated under reduced pressure. 4-(4-benzyl-piperazin-1-yl)-1H-indole (274 mg) was isolated as the hydrochloride salt from ethyl ether.
Method B

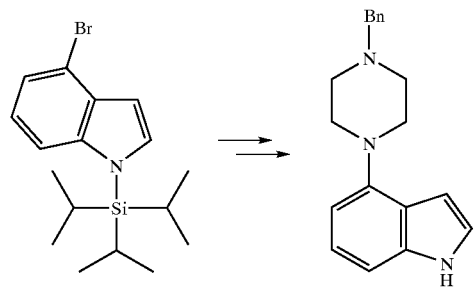

A mixture of 1.0 g (2.8 mmole) 4-bromo-triisopropylsilanyl-1H-indole, 0.54 mL (3.1 mmole) N-benzylpiperazine, 31 mg (0.14 mmole) palladium(II) acetate, 28 mg (0.14 mmole) tri-t-butylphosphine and 403 mg sodium t-butoxide in 5 mL xylene was heated at 120° for 15 hours. The reaction mixture was diluted with 100 mL 50% ether-hexane and filtered through a pad of silica gel 230–400 mesh. The filtrate was concentrated under reduced pressure to afford 1-triisopropylsilanyl-4-(4-benzyl-piperazin-1-yl)-1H-indole as a semi-solid, 1.2 g, M+H=448.

To a solution of 1.2 gram (2.68 mmole) 1-triisopropylsilanyl-4-(4-benzyl-piperazin-1-yl)-1H-indole in 20 mL tetrahydrofuran was added 3 mL (3 mmole) 1.0 M tetrabutylammonium fluoride in tetrahydrofuran. After 2 hours the solution was concentrated under reduced pressure and the residue was partitioned between 25 mL ethyl ether and 10 mL 10% sodium carbonate. The organic phase was washed with 3×10 mL water, dried (magnesium sulfate), and concentrated. 4-(4-Benzyl-piperazin-1-yl)-1H-indole was isolated as the white hydrochloride salt from ethyl ether, 604 mg, m.p. 233–234° C.

Step 2
4-(4-Benzyl-piperazin-1-yl)-1-(3,5-dichloro-benzenesulfonyl)-1H-indole

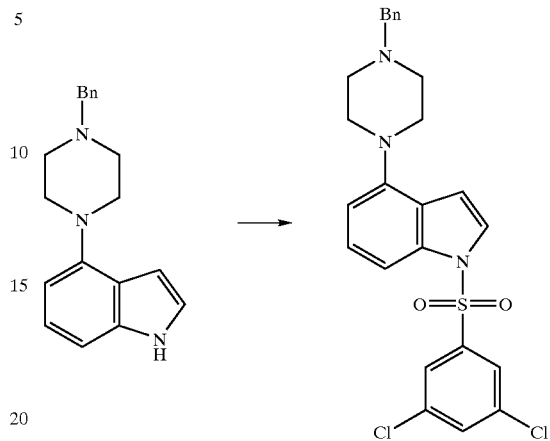

4-(4-Benzyl-piperazin-1-yl)-1H-indole (274 mg, 0.94 mmole) and 50 mg tetra-n-butylammonium hydrogen sulfate was stirred in a mixture of 10 mL toluene and 5 mL 4 N sodium hydroxide. Solid 3,5-dichlorobenzenesulfonyl chloride (246 mg, 1.0 mmole) was added in one portion. The reaction mixture was stirred at room temperature for 6 hours, then it was diluted with 20 mL water and extracted with 25 mL ethyl acetate. The organic phase was washed with 10 mL saturated sodium chloride solution, dried (magnesium sulfate) and concentrated. Recrystallization from dichloromethane provided 473 mg of 4-(4-benzyl-piperazin-1-yl)-1-(3,5-dichloro-benzenesulfonyl)-1H-indole, m.p. 201–203° C.

Similarly the following intermediates were prepared: 4-(4-benzyl-piperazin-1-yl)-1-(4-fluoro-benzenesulfonyl)-1H-indole, m.p. 162–163° C.; 4-(4-benzyl-piperazin-1-yl)-1-(4-methoxy-benzenesulfonyl)-1H-indole, m.p. 151–152° C.

Step 3
1-(3,5-Dichloro-benzenesulfonyl)-4-piperazin-1-yl-1H-indole.(2)

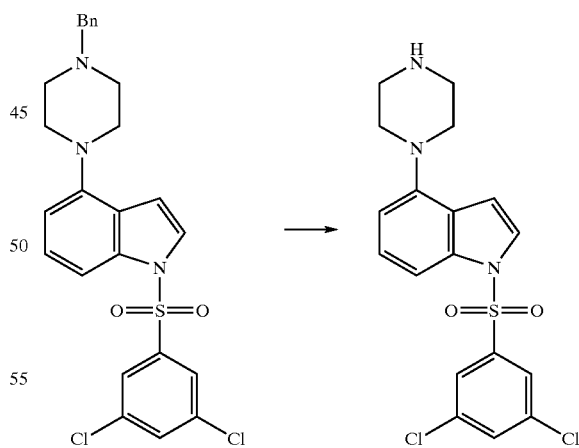

A solution of 0.1 g (0.2 mmole) 4-(4-benzyl-piperazin-1-yl)-1-(3,5-dichloro-benzenesulfonyl)-1H-indole and 0.05 mL (0.46 mmole) 1-chloroethyl chloroformate in 10 mL 1,2-dichloroethane was heated under reflux for 0.5 hour. The solution was concentrated under reduced pressure and the residue was dissolved in 6 mL methanol. The solution was heated under reflux for 1 hour, then it was concentrated. 1-(3,5-Dichloro-benzenesulfonyl)-4-piperazin-1-yl-1H-indole (2) was isolated as the hydrochloride salt from methanol/ethyl ether, 74 mg, M+H=410, m.p. 156–157° C.

Example 3

1-(4-Methoxy-benzenesulfonyl)-4-piperazin-1-yl-1H-indole(3)

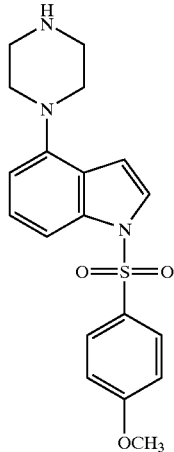

A mixture of 250 mg(0.54 mmole) 4-(4-benzyl-piperazin-1-yl)-1-(4-methoxybenzenesulfonyl)-1H-indole, 500 mg (8 mmole) ammonium formate and 50 mg 10% Pd-C in 20 mL ethanol was heated under reflux for 2 hours. The mixture was filtered through Whatman GF/B and the filtrate was concentrated under reduced pressure. The residue was partitioned between 10 mL 10% sodium carbonate and 25 mL ethyl acetate. The organic phase was washed with 5 ml water, 5 mL saturated sodium chloride, dried (magnesium sulfate) and concentrated under reduced pressure. The 1-(4-Methoxy-benzenesulfonyl)-4-piperazin-1-yl-1H-indole (3) was isolated as the hydrochloride salt from methanol-ethyl acetate-ether, 128 mg, m.p. 209–210° C.

Similarly the following compound was made from the intermediate in Example 2 Step 2:

1-(4-fluoro-benzenesulfonyl)-4-piperazin-1-yl-1H-indole (4) m.p. 203–204° C. as dihydrochloride salt.

Example 4

1-Benzenesulfonyl-4-piperazin-1-yl-1H-indole (5)

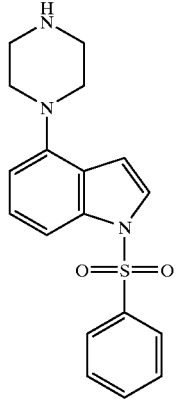

Step 1

4-(1-Benzenesulfonyl-1H-indol-4-yl)-piperazine-1-carboxylic acid tert-butyl ester

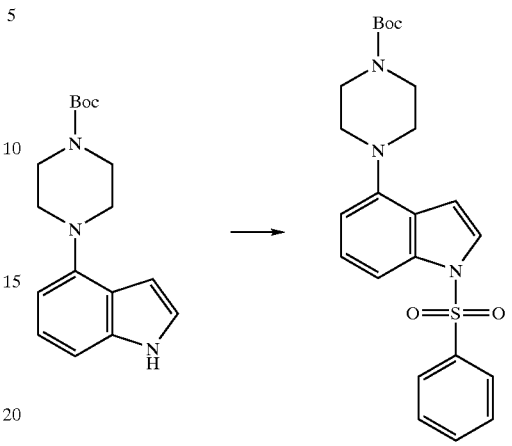

A mixture of 165 mg (0.55 mmole) 4-(1H-indol-4-yl)-piperazine-1-carboxylic acid tert-butyl ester, 25 mg tetrabutylammonium hydrogen sulfate and 0.08 mL (0.6 mmole) benzenesulfonyl chloride in 2 mL 4 M sodium hydroxide and 5 mL toluene was stirred at room temperature for 2 hours. The mixture was diluted with 5 mL water and extracted with 25 mL ethyl acetate. The organic phase was washed with 5 mL water, 5 mL saturated sodium chloride, dried (magnesium sulfate) and concentrated. 4-(1-Benzenesulfonyl-1H-indol-4-yl)-piperazine-1-carboxylic acid tert-butyl ester was isolated by recrystallization from ether/hexane, 223 mg, m.p. 143–144° C.

Step 2

1-Benzenesulfonyl-4-piperazin-1-yl-1H-indole

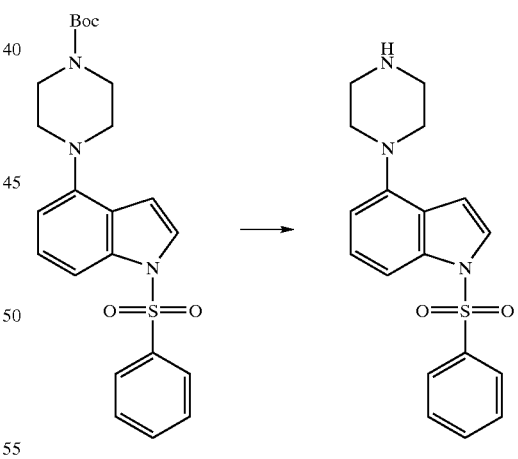

A solution of 125 mg (0.28 mmole) 4-(1-benzenesulfonyl-1H-indol-4-yl)-piperazine-1-carboxylic acid tert-butyl ester in 2 mL trifluoroacetic acid was stored at room temperature for 10 minutes. The solution was concentrated under reduced pressure and the residue was partitioned between 3 mL 10% sodium carbonate and 20 mL ethyl acetate. The organic phase was washed with 5 mL water, dried (magnesium sulfate) and concentrated. 1-Benzenesulfonyl-4-piperazin-1-yl-1H-indole (5) was isolated as the hydrochloride salt from ethyl acetate-ethyl ether, 73 mg, M+H=342; m.p.294–295° C.

Similarly following the procedure of Example 4 the following compounds were prepared:

1-(3-bromo-benzenesulfonyl)-4-piperazin-1-yl-1H-indole (6), M+H=420; m.p.158–159° C. as the hydrochloride salt;
4-piperazin-1-yl-1-(3-trifluoromethyl-benzenesulfonyl)-1H-indole (7), M+H=410; m.p.256–257° C. as the hydrochloride salt;
4-piperazin-1-yl-1-(thiophene-2-sulfonyl)-1H-indole (8), m.p.208–209° C. as trifluoroacetate salt;
1-(4-ter-butyl-benzenesulfonyl)-4-piperazin-1-yl-1H-indole (9), mp 231–232° C. (dec.) as trifluoroacetate salt;
1-(4-methanesulfonyl-benzenesulfonyl)-4-piperazin-1-yl-1H-indole (10), mp 234–235° C. (dec.) as trifluoroacetate salt;
1-(2,5-dichloro-benzenesulfonyl)-4-piperazin-1-yl-1H-indole (11), mp 237–238° C. (dec.) as trifluoroacetate salt;
1-(3-fluoro-benzenesulfonyl)-4-piperazin-1-yl-1H-indole (12), mp 227–228° C. (dec.) as trifluoroacetate salt;
1-(4-chloro-benzenesulfonyl)-4-piperazin-1-yl-1H-indole(1 3), mp 193–194° C. as trifluoroacetate salt;
1-(2,5-dimethoxy-benzenesulfonyl)-4-piperazin-1-yl-1H-indole (14), mp 245–246° C. (dec.) as trifluoroacetate salt;
1-(3-methoxy-benzenesulfonyl)-4-piperazin-1-yl-1H-indole (15), mp 221° C. (dec.) as trifluoroacetate salt;
1-(3-chloro-benzenesulfonyl)-4-piperazin-1-yl-1H-indole (16), 234–235° C. (dec.) as trifluoroacetate salt;
1-(3-methanesulfonyl-benzenesulfonyl)-4-piperazin-1-yl-1Hindole (17), 202–203° C. as trifluoroacetate salt;
1-(3-bromo-5-methanesulfonyl-benzenesulfonyl)-4-piperazin-1-yl-1H-indole (18), 181–182° C. as trifluoroacetate salt;
1-(5-bromo-6-chloro-pyridine-3-sulfonyl)-4-piperazin-1-yl-1H-indole (19), 199–200 (dec) as trifluoroacetate salt;
1-(2-fluoro-benzenesulfonyl)-4-piperazin-1-yl-1H-indole (20), mp 231–232° C. (dec.); NN-dimethyl-3-(4-piperazin-1-yl-indole-1-sulfonyl)-benzenesulfonamide (21), M+=449;
N-cyclopropyl-3-(4-piperazin-1-yl-indole-1-sulfonyl)-benzenesulfonamide (22), M+=461;
1-(2-fluoro-5-methanesulfonyl-benzenesulfonyl)-4-piperazin-1-yl-1H-indole (23), mp 172–173° C. (dec.) as trifluoroacetate salt;
3-(4-piperazin-1-yl-indole-1-sulfonyl)-benzonitrile (24), mp 238° C. (dec.) as trifluoroacetate salt;
1-(2-methanesulfonyl-benzenesulfonyl)-4-piperazin-1-yl-1H-indole (25), mp 171° C.; as trifluoroacetate salt;
1-[3-(2-methyl-propane-1-sulfonyl)-benzenesulfonyl]-4-piperazin-1-yl-1H-indole (26) mp 220–222° C. as trifluoroacetate salt;
1-(3-ethanesulfonyl-benzenesulfonyl)-4-piperazin-1-yl-1H-indole (27), mp 166–167° C., as hydrochloride salt;
4-piperazin-1-yl-1-[3-(propane-1-sulfonyl)-benzenesulfonyl]-1H-indole (28). mp 173–174° C. as trifluoroacetate salt;
1-(2,6-difluoro-benzenesulfonyl)-4-piperazin-1-yl-1H-indole, (29) mp 223–224° C., as trifluoroacetate salt; and
1-(1-Methyl-1H-imidazole-4-sulfonyl)-4-piperazin-1-yl-1H-indole, (30)). mp 230–231° C., as trifluoroacetate salt.

Example 4 A (Alternative)

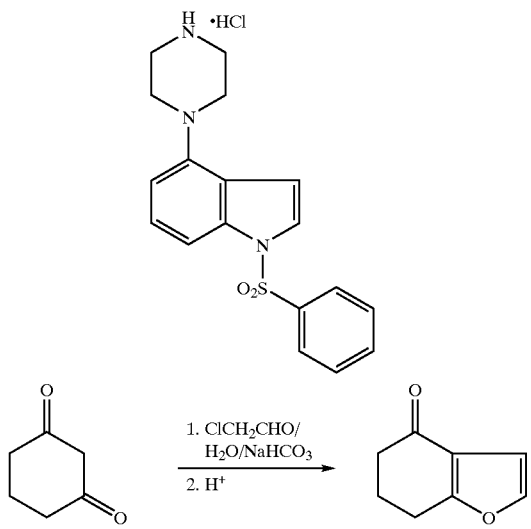

To a mixture of sodium bicarbonate (10.0 g, 0.12 mol) in water (80 ml) cooled in an ice bath was added 45% aqueous chloroacetaldehyde solution (17.7 ml, 0.122 mol). A solution of 1,3-cyclohexanedione (11.2 g, 0.1 mol) in water (90 ml) was then added over about 4 hours. The mixture was allowed to warm to room temperature and stirred overnight. After sampling for HPLC the reaction was diluted with ethyl acetate (100 ml). The pH was adjusted to about 1.2 with 50% sulfuric acid (30 ml). After stirring for 1 hour at room temperature the aqueous phase was separated. The organic phase was washed with a mixture of 50% sulfuric acid (25 ml) and water (50 ml), followed by saturated sodium carbonate solution (50 ml). The aqueous phases were sequentially backwashed with ethyl acetate. The combined organic extracts were filtered and evaporated to dryness to give a red oil (11 g). The residue was taken up in methylene chloride (25 ml) and hexane (25 ml) and stirred with silica gel (20 g). After 2 hours the silica gel was filtered off and washed with 50% methylene chloride/hexane (50 ml). Evaporation to dryness gave an oil (9.25 g, 68% yield). NMR: 7.32 2H d, 6.67 2H d, 2.89 2H t, 2.51 2H t, 2.18 2H m.

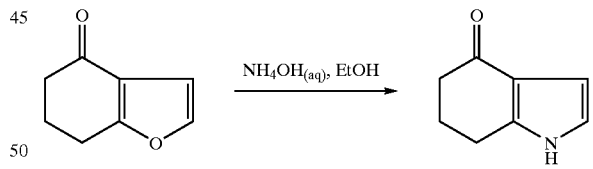

A mixture of 6,7-Dihydro-5H-benzofuran-4-one (9.25 g, 67.9 mmol), 30% ammonia solution (60 ml, 940 mmol) and reagent alcohol (25 ml) was heated in a sealed vessel in a 140 to 150° C. oil bath for 17 hours. After cooling the mixture was sampled for HPLC, and diluted with reagent alcohol (25 ml). A 10-ml aliquot was evaporated to dryness, diluted with 5% isopropyl alcohol/methylene chloride (20 ml) and applied to a silica gel pad (2.0 g). Elution with 5% isopropyl alcohol/methylene chloride (80 ml total) and evaporation to dryness gave 0.73 g of a yellow solid.

Another 10-ml aliquot was treated with Darco KB activated carbon (0.5 g) for 2 hours at room temperature. The carbon was filtered off and washed with 50% aqueous alcohol (10 ml). The filtrate was concentrated to about 3 g, diluted with water (10 ml), heated to the reflux and allowed to cool whereupon the product crystallized. The 1,5,6,7-

Tetrahydro-indol-4-one was filtered off, washed with water is (1 ml) and dried under vacuum at about 70 □ C. to give 0.46 g of a tan solid. NMR: 8.74 1H br, 6.68 2H dd, 6.56 2H dd, 2.83 2H t, 2.49 2H t, 2.16 2H m.

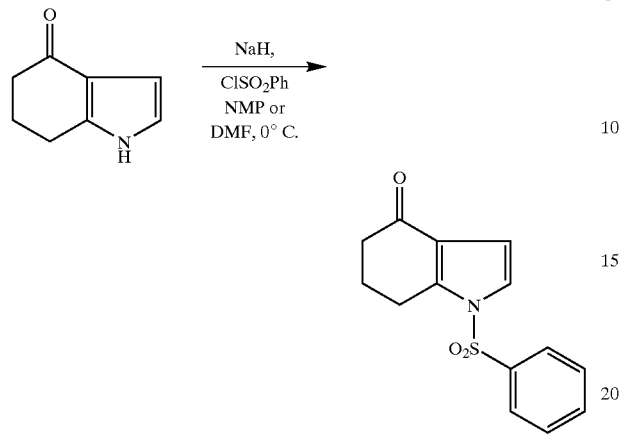

A mixture of 1,5,6,7-Tetrahydro-indol-4-one (25.3 g, 184 mmol), and DMF (125 ml) was stirred under nitrogen and cooled to 5–6° C. This mixture was treated with NaH (8.1 g, 202.4 mmol of a 60% dispersion in mineral oil) and allowed to warm to room temperature over about 1 hour. The mixture was recooled to 5–6° C. and treated with benzenesulfonyl chloride (33 g, 194 mmol). The mixture was warmed to room temperature over about 1 hour and treated in a dropwise manner with water (200 mL) with vigorous stirring. The solid so precipitated was collected by filtration and washed subsequently with water (200 mL) followed by hexanes (100 mL). The solid was air dried and placed in a vacuum oven for 14 hours at 50–55° C. with a nitrogen bleed. A total of 47.24 g of solid 1-benzenesulfonyl-1,5,6,7-tetrahydro-indol-4-one was recovered.

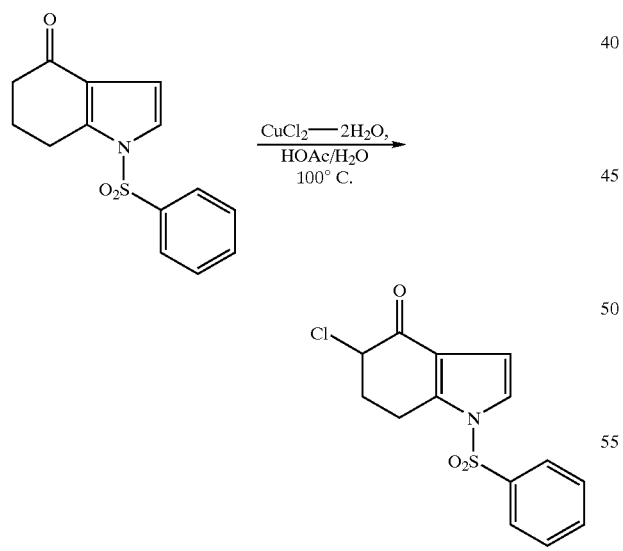

A mixture of 1-benzenesulfonyl-1,5,6,7-tetrahydro-indol-4-one (56.55 g, 200 mmol), CuCl2-2H2O (77.12 g, 450 mmol) was degassed under vacuum/nitrogen purge and stirred in a 1:1 HOAc/H2O solvent mixture (1000 mL total) which was also degassed under vacuum/nitrogen purge. This mixture was stirred at 100–101° C. for 18 hours. It was then cooled to 5–6° C., stirred and the solid collected by filtration.

This solid was digested off of the filter with hot (>70° C.) ethyl acetate (700 mL) to dissolve the product. The solution was polish filtered and concentrated in vacuo to a total volume of about 200 mL. The solid product was collected by filtration, washed with hexanes (300 mL) and dried in vacuo to afford 41.03 g 1-benzenesulfonyl-5-chloro-1,5,6,7-tetrahydro-indol-4-one.

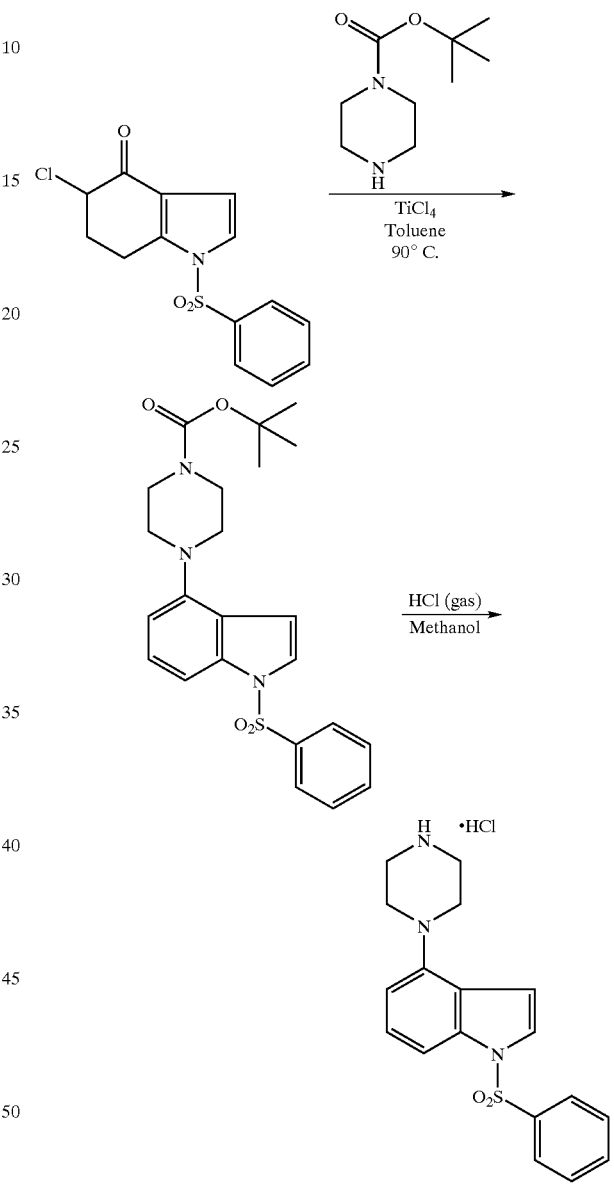

Titanium tetrachloride (8 ml 13.77 g) dissolved in toluene (65 ml) was added to piperazine-1-carboxylic acid tert-butyl ester (48 g) dissolved in toluene (363 ml) at 0–5° C. over about 10 minutes. The green reaction mixture was stirred for 10 minutes. 1-Benzenesulfonyl-5-chloro-1,5,6,7-tetrahydro-indol-4-one (14.52 g, 46.28 mM) was dissolved in warm toluene (400 ml) and then added to the reaction mixture over about 15 minutes below 15° C. The reaction mixture was heated to 90° C. for 2 hours. Analysis by TLC (30% ethyl acetate/hexane) showed that the reaction was complete. The reaction mixture was cooled to 20° C. and filtered through Celite. The solvent was distilled to a small volume (~300 ml) and the residual solvent displaced with methanol 500 ml.

Hydrogen chloride gas (29 g) was passed into the reaction solution and the reaction mixture concentrated to about 250 ml under vacuum over about half an hour. The reaction mixture was cooled in an ice bath to 0–5° C. The product was collected by filtration and dried under vacuum with a nitrogen bleed. Yield of 1-benzenesulfonyl-4-piperazin-1-yl-1H-indole hydrochloride was 14.12 g Mp: 275.6–285.6° C.

Example 5

1-Benzenesulfonyl-3-bromo-4-piperazin-1-yl-1H-indole

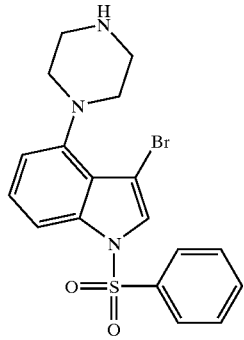

Step 1

4-(3-Bromo-1H-indol-4-yl)-piperazine-1-carboxylic acid tert-butyl ester

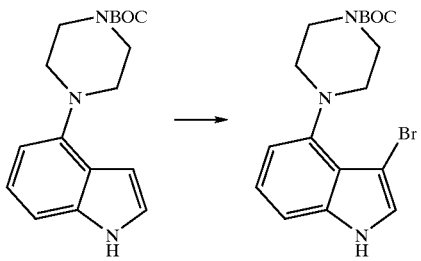

To an ice-cooled solution of 0.4 g (1.32 mmole) 4-(1H-indol-4-yl)-piperazine-1-carboxylic acid tert-butyl ester in 10 mL THF was added 0.83 mL (1.65 mmole) 2M n-butyl lithium in cyclohexane. The reaction mixture was stirred for 5 min and then cooled to −70° C. A solution of 0.26 g (1.44 mmole) N-bromosuccinimide in 6 mL THF was added and the mixture was stirred at 0° C. for 0.5 hr. The mixture was diluted with 10 mL water and extracted with 25 mL ether. The organic phase was washed with 5 mL water, dried (magnesium sulfate) and concentrated under reduced pressure. The residue was subjected to column chromatography over silica gel eluting with hexane/chloroform/ethyl acetate (50:48:2) to afford) 4-(3-bromo-1H-indol-4-yl)-piperazine-1-carboxylic acid tert-butyl ester as a foam, 0.46 g. Nmr (deuteriochloroform) ppm δ: 1.50 (s 9H), 3.08 (m, 4H), 3.71 (m, 4H), 6.72 (dd, 1H), 7.14 (m, 3H), 8.42 (brs, 1H).

Step 2

4-(1-Benzenesulfonyl-3-bromo-1H-indol-4-yl)-piperazine-1-carboxylic acid tert-butyl ester

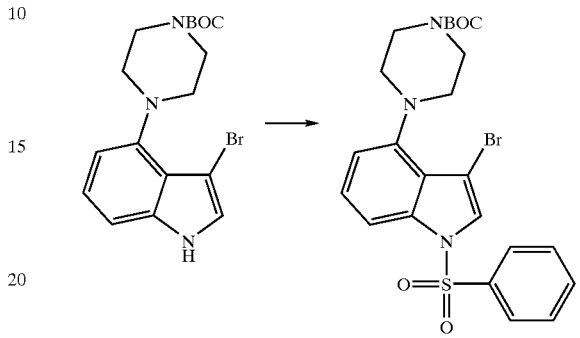

To a solution of 0.35 g (0.92 mmole) 4-(3-bromo-1H-indol-4-yl)-piperazine-1-carboxylic acid tert-butyl ester in 10 mL benzene was added 0.106 g (1.1 mmole) sodium t-butoxide and 0.19 g (1.1 mmole) benzenesulfonyl chloride. The reaction mixture was stirred at room temperature for 16 hrs. The mixture was washed with 2 mL water, dried (magnesium sulfate) and concentrated under reduced pressure. The residue was recrystallized from ethyl acetate/hexane to provide 0.42 g of 4-(1-benzenesulfonyl-3-bromo-1H-indol-4-yl)-piperazine-1-carboxylic acid tert-butyl ester, m.p. 188–189°.

Step 3

1-Benzenesulfonyl-3-bromo-4-piperazin-1-yl-1H-indole

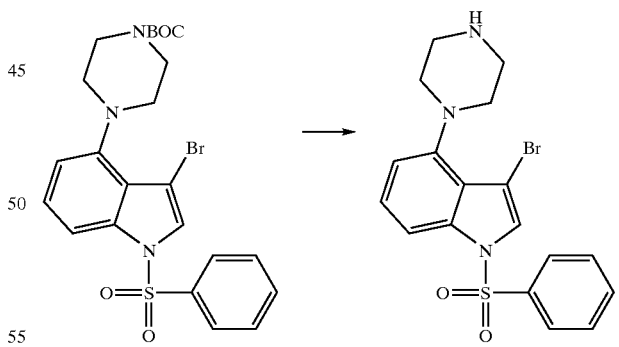

To a suspension of 0.102 g (0.2 mmole) 4-(1-benzenesulfonyl-3-bromo-1H-indol-4-yl)-piperazine-1-carboxylic acid tert-butyl ester in 3 mL ethanol was added 2 mL concentrated hydrochloric acid. The mixture was heated under reflux until all solid has dissolved. The mixture was concentrated to dryness under reduced pressure and the residue was recrystallized from methanol/ether to provide 0.082 g of 1-benzenesulfonyl-3-bromo-4-piperazin-1-yl-1H-indole (31), mp 304–305° C., as hydrochloride salt.

Example 6

1-(4-Fluoro-benzenesulfonyl)-4-(4-methyl-piperazin-1-yl)-1H-indole

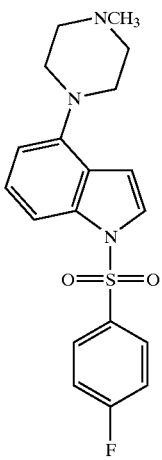

Step 1

4-(4-Methyl-piperazin-1-yl)-1H-indole dihydrochloride

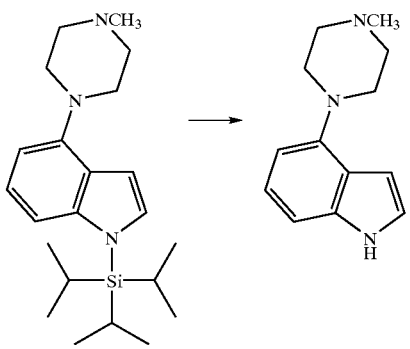

To a solution of 0.85 g (2.28 mmole) 1-triisopropylsilanyl-4-(4-methyl-piperazin-1-yl)-1H-indole in 25 mL THF was added 2.3 mL (2.3 mmole) 1.0M tetra-n-butyl ammonium fluoride in THF. The reaction mixture was stirred at room temperature for 2 hrs. The solution was concentrated under reduced pressure. The residue was partitioned between 5 mL 10% sodium carbonate and 25 mL ethyl acetate. The organic phase was washed with 5 mL saturated sodium chloride, dried (magnesium sulfate) and concentrated under reduced pressure. The dihydrochloride salt was recrystallized from methanol/ether to provide 0.465 g of 4-(4-methyl-piperazin-1-yl)-1H-indole dihydrochloride, m.p. 268–269° C. (dec.).

Step 2:
1-(4-Fluoro-benzenesulfonyl)-4-(4-methyl-piperazin-1-yl)-1H-indole

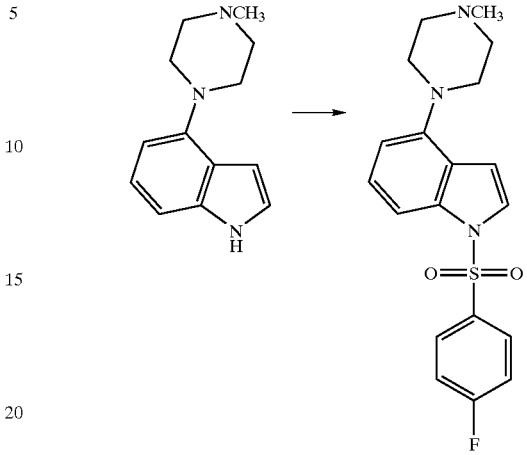

A mixture of 0.2 g (0.79 mmole) 4-(4-methyl-piperazin-1-yl)-1H-indole dihydrochloride, 0.2 g (1.03 mmole) 4-fluorobenzenesulfonyl chloride and 0.025 g tetrabutylammonium hydrogen sulfate in 5 mL 4M sodium hydroxide and 15 mL toluene was stirred at room temperature for 24 hrs. The mixture was diluted with 10 mL water and extracted with 25 mL ethyl acetate. The organic phase was washed with 5 mL water, 5 mL saturated sodium chloride, dried (magnesium sulfate) and concentrated under reduced pressure. The hydrochloride salt was recrystallized from ethyl acetate/ether to provide 0.208 g of 1-(4-fluoro-benzenesulfonyl)-4-(4-methyl-piperazin-1-yl)-1H-indole (32), m.p. 151–152° C.

Example 7

| Composition for Oral Administration | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 8

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 9

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Example 10

Parenteral Formulation (IV)

| Ingredient | % wt./wt. |
| --- | --- |
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 11

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 12

Topical Formulation

| Ingredients | grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 13

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 14

Radioligand Binding Studies

The binding activity of compounds of this invention in vitro was determined as follows.

Duplicate determinations of ligand affinity are made by competing for binding of [3H]LSD in cell membranes derived from HEK293 cells stably expressing recombinant human 5-HT6 receptor.

All determinations are made in assay buffer containing 50 mM Tris-HCl, 10 mM MgSO4, 0.5 mM EDTA, 1 mM ascorbic acid, pH 7.4 at 37° C., in a 250 microliter reaction volume. Assay tubes containing [3H] LSD (5 nM), competing ligand, and membrane are incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [3H] LSD is determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{B\text{max} - \text{basal}}{1 + 10^{-Hill(\log[ligand] - \log IC_{50})}} \right)$$

where Hill is the Hill slope, [ligand] is the concentration of competing radioligand and IC50 is the concentration of radioligand producing half-maximal specific binding of radioligand. The specific binding window is the difference between the Bmax and the basal parameters.

Proceeding as in Example 14, compounds of Formula I were tested and found to be selective 5-HT6 antagonists.

While the present invention has been described with reference to the specific embodiments thereof, it should be understood by those skilled in the art that various changes may be made and equivalents may be substituted without

What is claimed is:

1. A compound comprising Formula I:

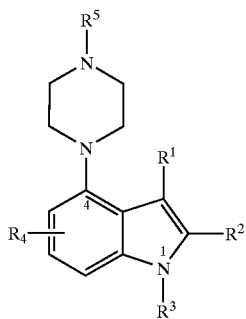

Formula I wherein:
- $R^1$ is selected from hydrogen, halo, haloalkyl, and $C_{1-6}$-alkyl;
- $R^2$ is selected from hydrogen, $C_{1-6}$-alkyl, $C_{1-6}$-alkoxy, and $C_{1-6}$-alkylthio;
- $R^3$ is $-SO_2-Ar$, and Ar is phenyl substituted with one aminosulfonyl;
- $R^4$ is selected from hydrogen, halogen, $C_{1-6}$-alkyl, $C_{1-6}$-alkoxy, $C_{1-6}$alkylthio, trifluoromethyl, cyano, and acyl; and
- $R^5$ is selected from hydrogen, $C_{1-6}$-alkyl and benzyl; or pharmaceutically acceptable salts thereof.

2. The compound of claim 1, wherein $R^1$ is hydrogen or halo.

3. The compound of claim 2, wherein $R^2$ is hydrogen.

4. The compound of claim 1 selected from:
NN-dimethyl-3-(4-piperazin-1-yl-indole-1-sulfonyl)-benzenesulfonamide; or
N-cyclopropyl-3-(4-piperazin-1-yl-indole-1-sulfonyl)-benzenesulfonamide.

5. A pharmaceutical composition comprising a therapeutically effective amount of at least one compound of claim 1 in admixture with at least one pharmaceutically acceptable carrier.

6. A method of treating a subject that has depression or psychosis, wherein said method comprises administering to said subject a therapeutically effective amount of the compound of claim 1.

7. A process for preparing a compound as claimed in claim 1 which comprises
treatment of a compound of formula I

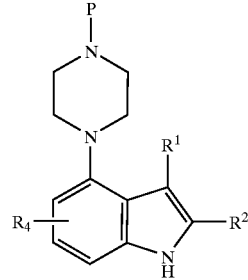

Formula f wherein P is a protective group and $R^1$, $R^2$ and $R^4$ are as defined in claim 1,
with an arylsulfonylhalide of Formula $Ar-SO_2-Hal$ wherein Hal is a halogen, and
Ar is as defined in claim 1,
followed by deprotection,
to provide a compound of the general Formula I:

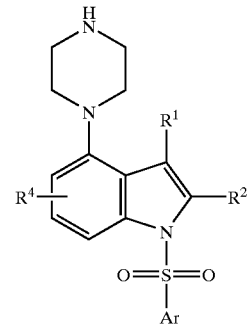

Formula I wherein Ar, $R^1$, $R^2$, and $R^4$ are as defined in claim 1.

* * * * *

UNITED STATES PATENT AND TRADEMARK OFFICE
CERTIFICATE OF CORRECTION

PATENT NO. : 6,790,848 B2
DATED : September 14, 2004
INVENTOR(S) : Andrew John Briggs et al.

It is certified that error appears in the above-identified patent and that said Letters Patent is hereby corrected as shown below:

Column 35,
Line 29, "substituted with one aminosulfonyl;" should read -- substituted with aminosulfonyl --;

Column 36,
Line 7, "compound of formula I" should read -- compound of formula f, --.

Signed and Sealed this

Third Day of May, 2005

JON W. DUDAS
*Director of the United States Patent and Trademark Office*